United States Patent
Kupzig et al.

(10) Patent No.: US 6,515,491 B1
(45) Date of Patent: Feb. 4, 2003

(54) STRUCTURAL BODY HAVING A STOCHASTIC SURFACE PATTERNING AS WELL AS A CAPACITIVE SENSOR HAVING SUCH A STRUCTURAL BODY

(75) Inventors: Michael Kupzig, Gerlingen (DE); Andrea Schilp, Schwaebisch Gmuend (DE); Karsten Funk, Palo Alto, CA (US)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 09/569,212

(22) Filed: May 11, 2000

(30) Foreign Application Priority Data

May 11, 1999 (DE) .......................... 199 21 847

(51) Int. Cl.[7] .................. G01R 27/26; G01R 27/08
(52) U.S. Cl. .................. 324/686; 324/696; 324/698
(58) Field of Search ................. 324/686, 698, 324/695, 696, 699, 71.1, 690; 361/290, 292, 303, 285; 438/964; 216/11

(56) References Cited

U.S. PATENT DOCUMENTS

| | | | |
|---|---|---|---|
| 5,090,932 A | * | 2/1992 | Dieumegard et al. .......... 216/11 |
| 5,317,252 A | * | 5/1994 | Kranbuehl .................. 324/71.1 |
| 5,846,870 A | * | 12/1998 | Ishida et al. ................ 438/398 |
| 5,963,833 A | * | 10/1999 | Thakur ....................... 438/677 |

\* cited by examiner

Primary Examiner—Christine Oda
Assistant Examiner—Anjan K. Deb
(74) Attorney, Agent, or Firm—Kenyon & Kenyon

(57) ABSTRACT

A structural body which, at least region-wise, has at least one area which is in contact with a liquid or a gas flowing past, and which, at least to a great extent, is provided with a surface patterning made of a plurality of randomly or irregularly distributed geometric forms, in particular pyramids. At least one such structural body be used in a capacitive sensor with which, in particular, the dielectric constants or the conductance of a liquid or a gas can be determined.

16 Claims, 2 Drawing Sheets

STRUCTURAL BODY HAVING A STOCHASTIC SURFACE PATTERNING AS WELL AS A CAPACITIVE SENSOR HAVING SUCH A STRUCTURAL BODY

FIELD OF THE INVENTION

The present invention relates to a structural body having a stochastic surface patterning, as well as a capacitive sensor having a structural body.

BACKGROUND INFORMATION

The measurement of dielectric constants, or even of the conductance, can be used for determining chemical substance properties. Thus, in cleaning processes, for example, the success of the cleaning can be inferred from the conductance of the washing liquid, or the composition of chemical compounds or mixtures such as of diesel fuels can be ascertained by measuring the dielectric constants.

In many cases, sensors for ascertaining these electrical properties of liquids and gases are composed of capacitor arrangements having interdigital comb structures, as are shown in FIG. 1. In this context, two electrodes are located opposite each other at a defined distance, while the substance to be analyzed is located in the interspace formed between them. In the practical case, the interspace is frequently implemented by slits having a constant spacing. The smaller the spacing of the slits, the more accurate the measurement becomes.

If the medium to be examined contains an impurity such as a coarse dust particle having a size in the order of magnitude of the interspace or greater, then this impurity will become caught on the electrodes, so that on one hand, the measuring result is invalidated, and on the other hand, the sensor is badly affected with time. It may be that the sensor can be cleaned by rinsing in the reverse direction, but many times jammed particles are not even removed with these means. In this respect, one must always expect a deterioration of the sensor. Finally, the sensor must either be disassembled for a rinsing, or the measuring system must have additional structural components for a rinse-solution pump.

Michael Köhler, in "*Ätzverfahren für die Mikroelektronik*" (Etching Methods for Microelectronics), 1998, WILEY-VCH Publishing House, particularly pages 322 ff., has already described methods for producing a stochastic distribution of differently formed pyramids on a surface of a material. From this, it is known in particular to produce a stochastic pyramidal surface patterning on a silicon wafer by a treatment with diluted KOH solution.

SUMMARY OF THE INVENTION

Compared to the related art, the structural body of the present invention having a stochastic surface patterning and the capacitive sensor of the present invention having such a structural body have the advantage that on one hand, because of the inhomogeneous electric flux lines resulting in response to the application of a voltage, a surface patterning of this type has a very high capacitance which is useful for exact measurements, and on the other hand, the surface patterning exhibits particularly good self-cleaning effects which are produced by the irregular spacings, arrangements and geometries of the multitude of geometric forms.

This self-cleaning effect is comparable to the cleaning effect of a fast-flowing water. Because of the irregular surface of the patterned areas, a medium flowing past does not exhibit a homogeneous flow distribution, e.g. within a channel, but rather fast-flowing regions and small swirls are formed. If a particle is now rinsed into the channel and is caught on a geometric form, the flow profile changes immediately and the particle is swirled around the geometric form. Thus, it "by-passes" this obstruction automatically.

Because of the randomly patterned area having a plurality of randomly or irregularly distributed geometric forms, enlargements always exist, both in the direction of flow and transverse thereto, through which corresponding swirls flow.

A surface patterning provided with a plurality of randomly or irregularly distributed geometric forms can also be used very advantageously in a capacitive sensor having a capacitor, the structural body or bodies being used in particular as capacitor plates which are in contact with a liquid or with a gas flowing past the surface.

Thus, it is very advantageous if the geometric forms in question have surface areas, heights or geometries varying as much as possible among each other and/or at least some of the geometric forms also partially overlap each other.

It is particularly expedient if, at least to a large extent, the geometric forms are pyramids. In this case, for example, electric flux lines run advantageously from pyramidal point to pyramidal point. Furthermore, the structural body is advantageously made of silicon, at least on the surface.

Moreover, the capacitive sensor of the present invention is very advantageously a plate-type capacitor whose capacitor plates are formed by two structural bodies according to the present invention which are each provided with a stochastic surface patterning along which a liquid or a gas flows. Such a sensor is very advantageously suited for analyzing the electric properties, in particular the dielectric constants or the conductance, of a multitude of different liquids or gases.

For that purpose, the sensor is advantageously provided, at least region-wise, with an electric contact, particularly a metallization of the structural body. Also advantageously provided is an electronic evaluation circuit which is connected to the capacitor and, in a manner known per se, ascertains a physical measurable quantity from which the dielectric constants and/or the conductance of the liquid or the gas, which in particular is flowing past, can be determined.

DETAILED DESCRIPTION

Figure 1:
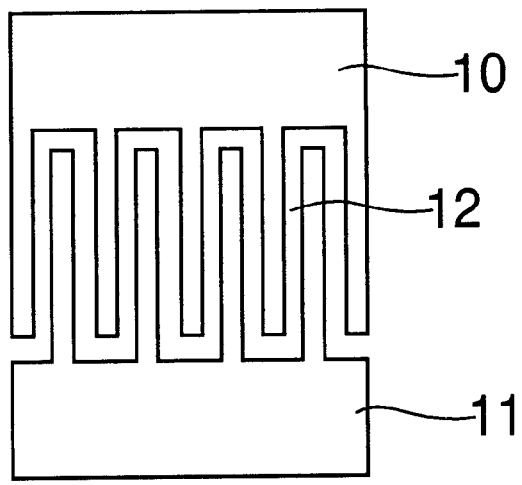
FIG. 1 shows a capacitor design known from the related art.

First of all, for the purpose of comparison, FIG. 1 shows a specific embodiment of an interdigital capacitor known from the related art, having a first electrode 10 and a second electrode 11 as well as an interspace 12, which can be used as a capacitive sensor for analyzing liquids or gases.

Figure 2:
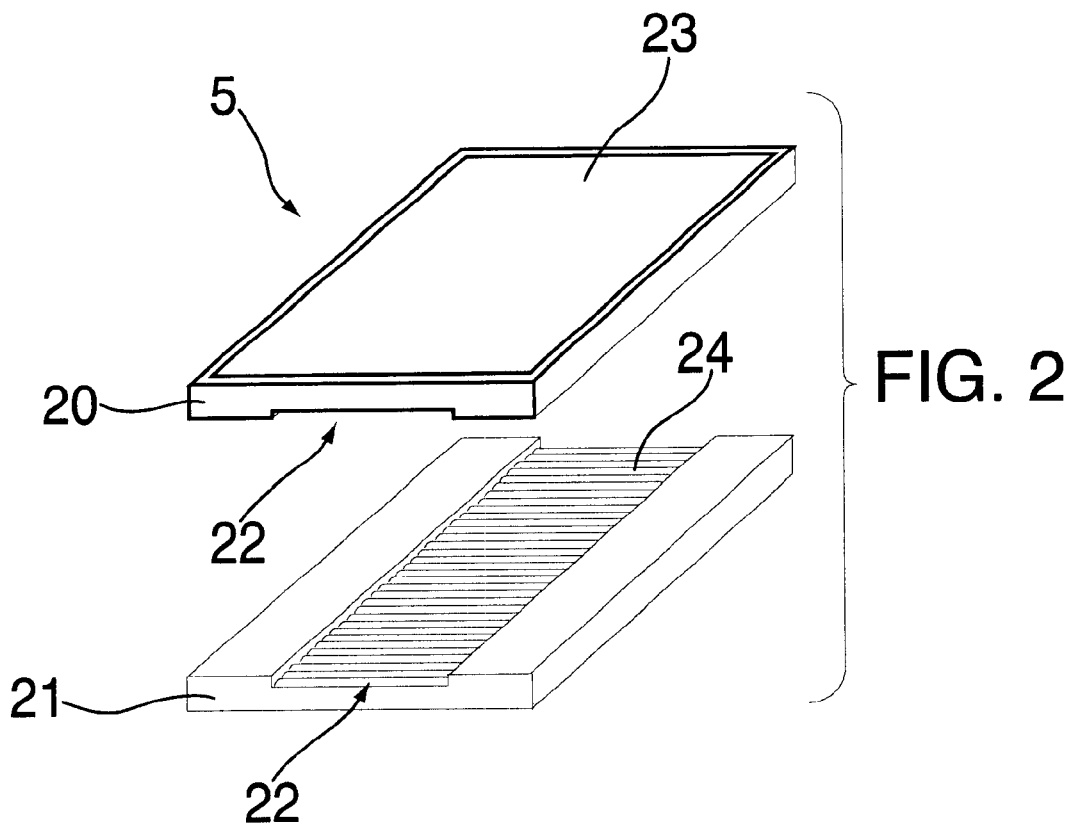
FIG. 2 shows a capacitor design of the present invention for a capacitive sensor having two structural bodies lying opposite each other.

FIG. 2 shows an exemplary embodiment of the invention, in which two substantially identical planar structural bodies 20, 21, which have been patterned out in a generally known manner from a silicon wafer, are lying opposite each other. Each of the two structural bodies 20, 21 has a size of, e.g. 2 mm×5 mm. Furthermore, a pocket is provided in each of the two structural bodies 20, 21, so that after the two structural bodies 20, 21 are brought together, a channel 22 is formed through which a liquid or a gas, e.g. water, organic hydrocarbon or fuels, is guided. Moreover, in the region of channel 20, each of the two structural bodies 20, 21 has at least one area which is provided with a surface patterning 24 composed of a plurality of randomly or irregularly distributed pyramids 25. These pyramids 25 have surface areas, heights or geometries which vary as much as possible and also partially overlap each other. Thus, the inside walls of channel 22 are formed essentially from areas patterned in this manner.

Surface patterning 24 was achieved in a manner known per se, by treating the silicon surface of structural bodies 20, 21 with a diluted KOH solution.

Depending on the selection of the material for structural bodies 20, 21 and the method used for producing surface patterning 24, besides or instead of pyramids 25, the stochastically distributed geometric forms produced can, however, also assume the form of circular cones or peaks, cylinders or similar shapes.

In each case on the side of structural bodies 20, 21 facing away from surface patterning 24, a possibility is provided for an electric contact, particularly a generally known metallization, on the surface of structural bodies 20, 21.

After forming the surface patterning, the two mutually opposing structural bodies 20, 21 were joined to form a capacitor 5 and insulated from each other at the contacting surfaces. This insulation is effected, for example, in a generally known manner by anodic bonding with an intermediate glass layer, by joining with a glass seal or solder glass or by another suitable adhesive technique using insulating adhesive. In this manner, channel 22 is formed which has a height of, e.g. 2 $\mu$m to 1 mm and whose inside walls are provided, at least to a great extent, with a surface patterning 24, and which are composed of a plurality of randomly distributed, irregular pyramids 25. In this context, channel 22 itself can have a largely arbitrary structure, i.e., it can be meander-shaped, for example, or can have an interdigital structure.

Figure 3:
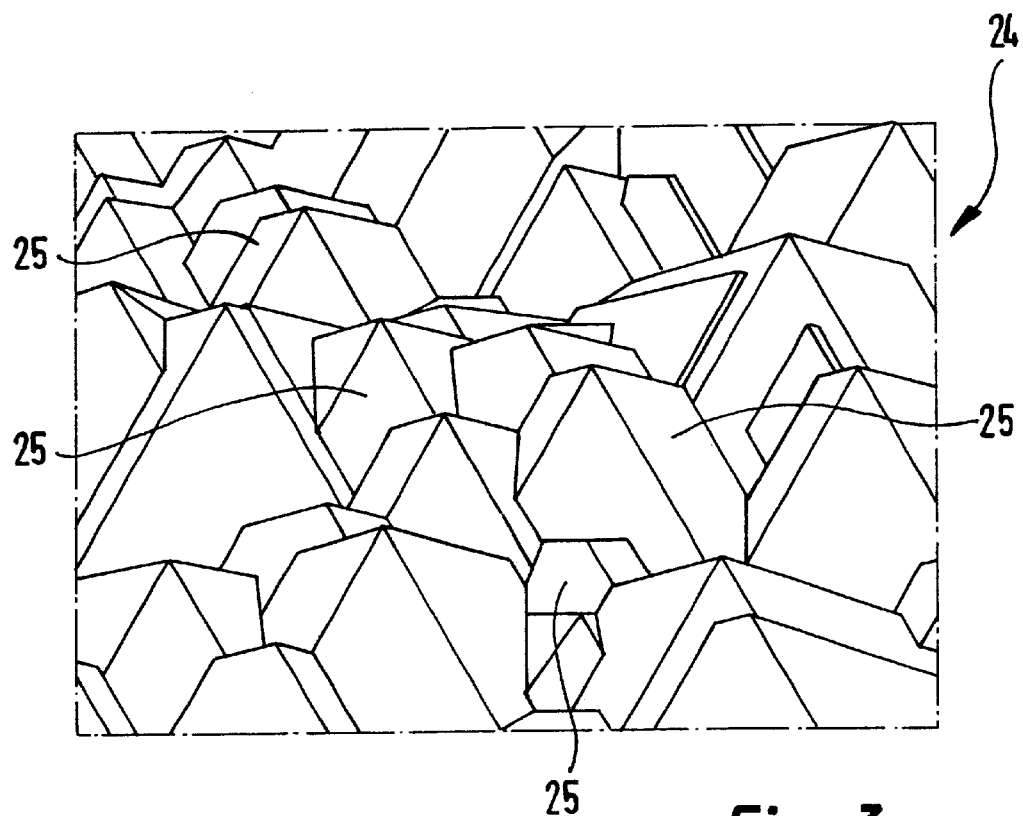
FIG. 3 shows a microscopic enlargement of a surface patterning of an area of the structural body according to FIG. 2.

FIG. 3 shows a microscopic segment of surface patterning 24 of an area of a structural body 20, 21 which forms an inside wall of channel 22. One can clearly see the irregularly distributed and formed pyramids 25 which have a typical size of approximately 3 $\mu$m to 15 $\mu$m.

Figure 4:
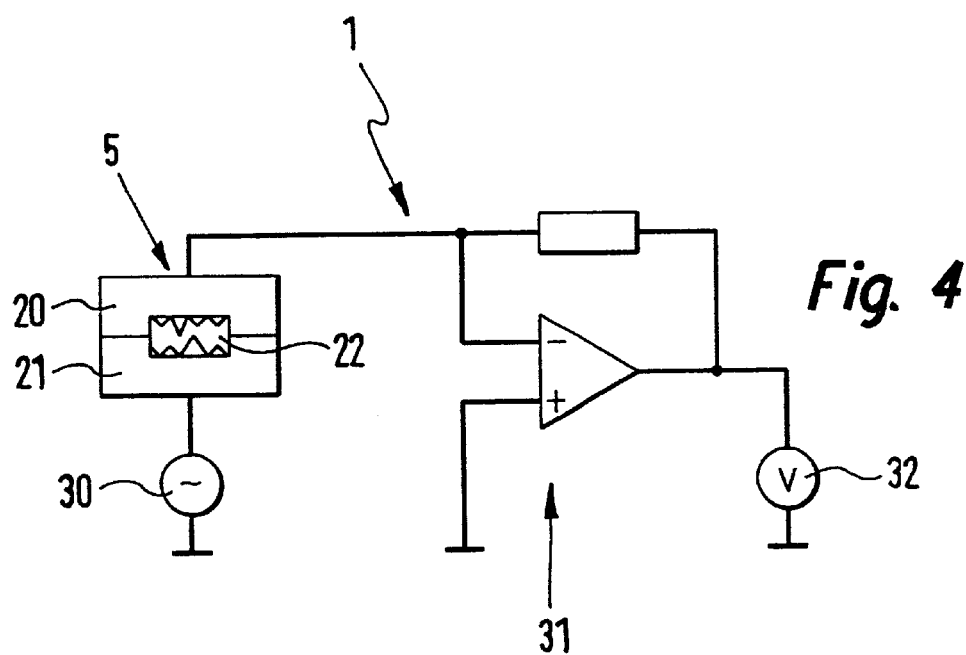
FIG. 4 shows a block diagram of a capacitive sensor having an evaluation circuit.

Finally, FIG. 4 shows a sensor 1 in the form of a capacitive sensor, in particular a capacitive fluid sensor, having a capacitor 5 in the form of a plate-type capacitor whose capacitor plates are formed by the two structural bodies 20, 21 previously explained. For example, a liquid such as water is guided through channel 22 and thus flows past the areas provided with surface patterning 24 and is in contact with them.

Also provided for sensor 1 is a voltage source 30, for example, a sinusoidal alternating voltage source, which feeds a current into capacitor 5, e.g. via metallizations 23, that can be measured with a generally known evaluation circuit 31, for example with the aid of a current-voltage transformer, and with a downstream measuring instrument 32.

Thus, sensor 1 can be used to ascertain a physical measurable quantity from which, for example, the dielectric constants and/or the conductance of the liquid or gas flowing through capacitor 5 can be determined as a function of time.

However, a gas or a liquid standing in capacitor 5 can obviously also be analyzed by sensor 1 of the present invention as a function of time with regard to the quantities indicated.

Reference Numeral List 1 sensor
5 capacitor
10 first electrode
11 second electrode
12 interspace
20 first structural body
21 second structural body
22 channel
23 metallization
24 surface patterning
25 pyramids
30 voltage source
31 evaluation circuit
32 measuring instrument

What is claimed is:

1. A structural body for a capacitance probe comprising:
at least one area that is in contact with a liquid flowing past the at least one area, wherein:
the at least one area is provided with a surface patterning formed of silicon and formed of a plurality of geometric forms that are one of randomly and irregularly distributed, at least one of the forms of the geometric forms being a pyramid.

2. The structural body according to claim 1, wherein:
the plurality of geometric forms have one of surface areas, heights, and geometries that vary among each other to a maximum extent.

3. The structural body according to claim 1, wherein:
at least some of the plurality of geometric forms partially overlap each other.

4. The structural body according to claim 1, wherein:
at least a surface of the at least one area is formed from silicon.

5. The structural body according to claim 1, wherein:
the liquid flows past the at least one area.

6. The structural body according to claim 1, wherein:
at least most of the plurality of geometric forms are pyramids.

7. A capacitive sensor, comprising:
at least one capacitor, including:
at least one structural body provided with at least one area which is in contact with one of a liquid and a gas flowing past the at least one area, wherein:
the at least one area is provided with a surface patterning formed of a plurality of geometric forms that are one of randomly and irregularly distributed.

8. The capacitive sensor according to claim 7, wherein:
the at least one structural body includes a first structural body and a second structural body,
the at least one capacitor is a plate-type capacitor including a plurality of capacitor plates formed by the first structural body and the second structural body, and
the one of the liquid and the gas flows along the surface patterning of the first structural body and the second structural body.

9. The capacitive sensor according to claim 7, wherein:
the plurality of geometric forms have one of surface areas, heights, and geometries that vary among each other to a maximum extent.

10. The capacitive sensor according to claim 9, wherein:
at least some of the plurality of geometric forms partially overlap each other.

11. The capacitive sensor according to claim 7, wherein:
at least a surface of the at least one area is formed from silicon.

12. The capacitive sensor according to claim 7, wherein:
the one of the liquid and the gas flows past the at least one area.

13. The capacitive sensor according to claim 7, wherein:
at least most of the plurality of geometric forms are pyramids.

14. The capacitive sensor according to claim 7, further comprising:

an electric contact provided at least region-wise on the at least one structural body.

15. The capacitive sensor according to claim 14, wherein:
the electric contact corresponds to a metallization of the at least one structural body.

16. The capacitive sensor according to claim 7, further comprising:

an electronic evaluation circuit connected to the at least one capacitor and for ascertaining a physical measurable quantity from which at least one of dielectric constants and a conductance of the one of the liquid and the gas can be determined.

* * * * *